US011478010B2

(12) United States Patent
Popa Nita et al.

(10) Patent No.: US 11,478,010 B2
(45) Date of Patent: Oct. 25, 2022

(54) NUTRITIONAL PRODUCTS TO PROMOTE SAFE SWALLOWING FOR INDIVIDUALS WITH DYSPHAGIA

(71) Applicant: NESTEC S.A., Vevey (CH)

(72) Inventors: Simina Florentina Popa Nita, Morges (CH); Jan Engmann, Lausanne (CH); Adam Burbidge, Arzier (CH); Marco Ramaioli, London (GB)

(73) Assignee: Societe des Produits Nestle S.A., Vevey (CH)

( * ) Notice: Subject to any disclaimer, the term of this patent is extended or adjusted under 35 U.S.C. 154(b) by 320 days.

(21) Appl. No.: 15/327,745

(22) PCT Filed: Jul. 20, 2015

(86) PCT No.: PCT/EP2015/066558

§ 371 (c)(1),
(2) Date: Jan. 20, 2017

(87) PCT Pub. No.: WO2016/012403

PCT Pub. Date: Jan. 28, 2016

(65) Prior Publication Data

US 2017/0196250 A1 Jul. 13, 2017

Related U.S. Application Data

(60) Provisional application No. 62/026,958, filed on Jul. 21, 2014.

(30) Foreign Application Priority Data

Jul. 21, 2014 (EP) .................................... 14177895

(51) Int. Cl.

| | |
|---|---|
| ***A23L 29/225*** | (2016.01) |
| ***A23L 33/00*** | (2016.01) |
| ***A23L 29/269*** | (2016.01) |
| ***A23L 7/10*** | (2016.01) |
| ***A61K 47/36*** | (2006.01) |
| ***A23L 33/10*** | (2016.01) |
| ***A23L 2/52*** | (2006.01) |

(52) U.S. Cl.

CPC ................ *A23L 33/40* (2016.08); *A23L 2/52* (2013.01); *A23L 7/115* (2016.08); *A23L 29/225* (2016.08); *A23L 29/271* (2016.08); *A23L 33/10* (2016.08); *A61K 47/36* (2013.01); *A23V 2002/00* (2013.01)

(58) Field of Classification Search

CPC .......... A23L 2/52; A23L 29/271; A23L 33/10; A23L 33/40

See application file for complete search history.

(56) References Cited

U.S. PATENT DOCUMENTS

| | | | | |
|---|---|---|---|---|
| 6,284,886 | B1 | 9/2001 | Redmond | |
| 10,582,722 | B2 * | 3/2020 | Burbidge | A23L 33/15 |
| 2002/0146448 | A1 * | 10/2002 | Kozbor | A61K 39/39 424/450 |
| 2003/0092165 | A1 * | 5/2003 | Aichinger | C12N 1/14 435/254.1 |
| 2006/0121131 | A1 | 6/2006 | Redmond et al. | |
| 2007/0224126 | A1 | 9/2007 | Dufresne et al. | |
| 2008/0311243 | A1 | 12/2008 | Vasanthan et al. | |
| 2010/0221265 | A1 * | 9/2010 | Sancho-Madrid | A61P 11/06 424/173.1 |
| 2012/0195873 | A1 * | 8/2012 | Miller | A61K 31/202 424/94.4 |
| 2013/0171317 | A1 * | 7/2013 | Chang | A23L 13/67 426/574 |

FOREIGN PATENT DOCUMENTS

| | | | | |
|---|---|---|---|---|
| WO | 02076244 | A1 | 10/2002 | |
| WO | 2006054886 | | 5/2006 | |
| WO | WO-2011152706 | A1 * | 12/2011 | A61K 35/20 |
| WO | 2012117065 | | 9/2012 | |
| WO | 2013087918 | | 6/2013 | |
| WO | 2016012403 | A1 | 1/2016 | |

OTHER PUBLICATIONS

"Curdlan Gum", http://www1.lsbu.ac.uk/water/curdlan.html, pp. 1-2. (Year: 2015).*

Lo et al., Chapter 22 Bioconversion of Whey Lactose into Microbial Exopolysaccharides, p. 559-583. (Year: 2007).*

Ishihara et al. "Swallowing profiles of food polysaccharide gels in relation to bolus rheology" Food Hydrocolloids, 2011, vol. 25, pp. 1016-1024.

Lazaridou et al., "A Comparative Study on Structure—Function Relations of Mixed-Linkage (1→3), (1→4) Linear β-D-Glucans", Food Hydrocolloids, vol. 18, Issue No. 5, 2004, pp. 837-855.

Havrlentova et al., "Cereal β-Glucans and their Significance for the Preparation of Functional Foods—A Review", Czech Journal of Food Science, vol. 29, Issue No. 1, 2011, pp. 1-14.

Ahmad et al., "Beta Glucan: A Valuable Functional Ingredient in Foods", Critical Reviews in Food Science and Nutrition, vol. 52, Issue No. 3, 2012, pp. 201-212.

Gallegos et al., "Rheology and Dysphagia: An Overview", Annual Transactions of the Nordic Rheology Society, vol. 20, 2012, pp. 3-10.

Fuente et al., "Rheological Aspects of Swallowing and Dysphagia: Shear and Elongational Flows", Dysphagia, 2017, 30 Pages.

(Continued)

*Primary Examiner* — Walter A Moore
(74) *Attorney, Agent, or Firm* — K&L Gates LLP

(57) ABSTRACT

Nutritional products, uses thereof, methods for the manufacture and methods for improving the cohesiveness of the nutritional products are disclosed. The nutritional products have improved cohesiveness for promoting safer swallowing of food boluses for individuals having swallowing difficulties such as dysphagia.

4 Claims, No Drawings

(56) References Cited

OTHER PUBLICATIONS

Anttila et al., "Viscosity of Beta-Glucan in Oat Products", Agricultural and Food Science, vol. 13, Issue No. 1, 2004, pp. 80-87.
"Beta-Glucan"—Wikipedia, Retrevied from (en.wikipedia.org/wiki/Beta-glucan), Dec. 21, 2021, 7 Pages.
Haward et al., "Shearand Extensional Rheology of Cellulose/lonic Liquid Solutions", Biomacromolecules, vol. 13, Issue No. 5, 2012, pp. 1688-1699.
Wendin et al., "Objective and Quantitative Definitions of Modified Food Textures Based on Sensory and Rheological Methodology", Food & Nutrition Research, vol. 54, Issue No. 1, 2010, pp. 1-11.
Bourbon et al., "Characterization of Galactomannans Extracted from Seeds of Gleditsia Triacanthos and Sophora Japonica through Shear and Extensional Rheology: Comparison with Guar Gum and Locust Bean Gum", Food Hydrocolloids, vol. 24, Issue No. 2-3, 2010, pp. 184-192.
Duxenneuner et al., "Extensional Properties of Hydroxypropyl Ether Guar Gum Solutions", Biomacromolecules, vol. 9, Issue No. 11, 2008, pp. 2989-2996.
Volman et al., "Dietary Modulation of Immune Function by β-glucans", Physiology & Behavior, vol. 94, Issue No. 2, 2008, pp. 276-284.
Lai et al., "Average Shear Rates in the Rapid Visco Analyser (RVA) Mixing System", Cereal Chemistry, vol. 77, Issue No. 6, 2000, pp. 714-716.
Nishinari et al., "Role of Fluid Cohesiveness in Safe Swallowing", Science of Food, vol. 3, Issue No 5, 2019, pp. 1-13.
"Determination of the Extensional Relaxation Time of a Yeast Beta-Glucan", Technical Report, Dec. 23, 2021, pp. 1-6.
European Patent Office Communication for Application No. 15738929.7-1105 / 3171708, dated Jan. 4, 2022, 52 pages.

* cited by examiner

NUTRITIONAL PRODUCTS TO PROMOTE SAFE SWALLOWING FOR INDIVIDUALS WITH DYSPHAGIA

CROSS REFERENCE TO RELATED APPLICATIONS

The present application is a National Stage of International Application No. PCT/EP2015/066558, filed on Jul. 20, 2015, which claims priority to U.S. Provisional Patent Application Ser. No. 62/026,958, filed Jul. 21, 2014, and European Patent Application No. 14177895.1, filed Jul. 21, 2014, the entire contents of which are being incorporated herein by reference.

FIELD OF INVENTION

The present disclosure is related to nutritional products, a use of the nutritional products, a method for making the nutritional products and a method for improving the cohesiveness of the nutritional products.

BACKGROUND OF INVENTION

Dysphagia is a medical term for the symptom of difficulty in swallowing. Dysphagia may be a sensation that suggests a difficulty in a passage of solids or liquids (i.e. nutritional products) from the mouth to the stomach.

During processing in the mouth and swallowing, a viscosity of the nutritional products changes due to shear forces. It is known that in most of the cases the viscosity of nutritional products decreases when the shear forces and rate acting on the nutritional products (e.g., chewing forces) increase. Individuals who suffer from dysphagia often require thickened nutritional products. Thickening of the nutritional products is achieved to increase the viscosity of the food product by adding thickeners such as starch or gum thickeners. The thickened nutritional products make it less likely that an individual with dysphagia will aspirate during passage of the nutritional products from the mouth to the stomach. Individuals with dysphagia may find that nutritional products cause coughing, spluttering or even choking and therefore thickened nutritional products enables the individuals who suffer from dysphagia to swallow safely. Although the addition of thickeners is thought to improve a bolus control and timing of swallowing, it is disliked by individuals who suffer from dysphagia due to the extra swallowing effort required and as the thickener leaves residues with high levels of viscosity resulting in undesirable organoleptic properties. Furthermore thickened nutritional products lack the cohesiveness that saliva provides to food boluses.

Epidemiological studies estimate a prevalence rate of 16% to 22% among individuals who suffer from dysphagia that are over 50 years of age.

Dysphagia is classified into three major types: oropharyngeal dysphagia, esophageal dysphagia and functional dysphagia.

Oropharyngeal dysphagia is generally not treatable with medication. Oropharyngeal dysphagia affects individuals of all ages, but is more prevalent in older individuals.

Worldwide, oropharyngeal dysphagia affects approximately 22 million people over the age of 50. Oropharyngeal dysphagia is often a consequence of an acute event such as a stroke, brain injury, or surgery for oral or throat cancer. In addition, radiotherapy and chemotherapy may weaken the muscles and degrade the nerves associated with the physiology and nervous innervation of the swallow reflex. Oropharyngeal dysphagia is also common for individuals with progressive neuromuscular diseases, such as Parkinson's disease, to experience increasing difficulty in swallowing initiation. Representative causes of oropharyngeal dysphagia include those associated neurological illnesses (brainstem tumors, head trauma, stroke, cerebral palsy, Guillain-Barre syndrome, Huntington's disease, multiple sclerosis, polio, post-polio syndrome, Tardive dyskinesia, metabolic encephalopathies, amyotrophic lateral sclerosis, Parkinson's disease, dementia), infectious illnesses (diphtheria, botulism, Lyme disease, syphilis, mucositis [herpetic, cytomegalovirus, *Candida*, etc.]), autoimmune illnesses (lupus, scleroderma, Sjogren's syndrome), metabolic illnesses (amyloidosis, cushing's syndrome, thyrotoxicosis, Wilson's disease), myopathic illnesses (connective tissue disease, dermatomyositis, myasthenia gravis, myotonic dystrophy, oculopharyngeal dystrophy, polymyositis, sarcoidosis, paraneoplastic syndromes, inflammatory myopathy), iatrogenic illnesses (medication side effects [e.g., chemotherapy, neuroleptics, etc.], post surgical muscular or neurogenic, radiation therapy, corrosive [pill injury, intentional]), and structural illnesses (cricopharyngeal bar, Zenker's diverticulum, cervical webs, oropharyngeal tumors, osteophytes and skeletal abnormalities, congenital [cleft palate, diverticulae, pouches, etc.]).

Esophageal dysphagia can affect individuals of all ages. Esophageal dysphagia is generally treatable with medications and is considered a less serious form of dysphagia. Esophageal dysphagia is often a consequence of mucosal, mediastinal, or neuromuscular diseases. Mucosal (intrinsic) diseases narrow the lumen through inflammation, fibrosis, or neoplasia associated with various conditions (e.g., peptic stricture secondary to gastroesophageal reflux disease, esophageal rings and webs [e.g., sideropenic dysphagia or Plummer-Vinson syndrome], esophageal tumors, chemical injury [e.g., caustic ingestion, pill esophagitis, sclerotherapy for varices], radiation injury, infectious esophagitis, and eosinophilic esophagitis). Mediastinal (extrinsic) diseases obstruct the esophagus by direct invasion or through lymph node enlargement associated with various conditions (tumors [e.g., lung cancer, lymphoma], infections [e.g., tuberculosis, histoplasmosis], and cardiovascular [dilated auricula and vascular compression]). Neuromuscular diseases may affect the esophageal smooth muscle and its innervation, disrupting peristalsis or lower esophageal sphincter relaxation, or both, commonly associated with various conditions (achalasia [both idiopathic and associated with Chagas disease], scleroderma, other motility disorders, and a consequence of surgery [i.e., after fundoplication and antireflux interventions]). It is also common for individuals with intraluminal foreign bodies to experience acute esophageal dysphagia.

Functional dysphagia is defined in some patients wherein no organic cause for dysphagia can be found.

Dysphagia is not generally diagnosed. Dysphagia has major consequences on health and healthcare costs on individuals who suffer from dysphagia. Individuals who suffer from severe dysphagia experience a sensation of impaired passage of nutritional products from the mouth to the stomach, occurring immediately after swallowing. Among community dwelling individuals, perceived symptoms may bring the individuals who suffer from dysphagia to see a doctor. Among institutionalized individuals, health care practitioners may observe symptoms or hear comments from the individuals who suffer from dysphagia or their family member suggestive of swallowing impairment and recommend the individuals who suffer from dysphagia be evaluated by a specialist. As the general awareness of swallowing impairments is low among front-line practitioners, dysphagia often goes undiagnosed and untreated. Yet, through referral to a swallowing specialist (e.g. speech language pathologist), a patient can be clinically evaluated and dysphagia diagnosis can be determined.

The general awareness of swallowing impairments is low among front-line practitioners. Many people (especially those who are elderly) suffer with undiagnosed and untreated swallowing impairments. One reason is that front-line community care practitioners (e.g., general practitioners/geriatricians, home care nurses, physical therapists, etc.) do not typically screen for the condition. If they are aware of the severity of swallowing impairments, they commonly do not use an evidence-based method of screening.

A severity of dysphagia may vary from: (i) minimal (perceived) difficulty in safely swallowing nutritional products, (ii) an inability to swallow nutritional products without significant risk for aspiration or choking, and (iii) a complete inability to swallow nutritional products. An inability to properly swallow nutritional products may be due to food boluses of the nutritional products being broken up into smaller fragments, which may enter the airway or leave unwanted residues in the oropharyngeal and/or esophageal tract during the swallowing process (e.g., aspiration). If enough material enters the lungs, it is possible that the patient may drown on the nutritional products that have built up in the lungs. Even small volumes of aspirated nutritional products may lead to bronchopneumonia infection, and chronic aspiration may lead to bronchiectasis and may cause some cases of asthma.

Silent aspiration is a common condition among the elderly and refers to the aspiration of the oropharyngeal contents during sleep. People may compensate for less-severe swallowing impairments by self-limiting the diet. The aging process itself, coupled with chronic diseases such as hypertension or osteoarthritis, predisposes the elderly to (subclinical) dysphagia that may go undiagnosed and untreated until a clinical complication such as pneumonia, dehydration, malnutrition (and related complications) occurs.

Dysphagia and aspiration impacts upon quality of life, morbidity and mortality. Twelve-month mortality is high (45%) among individuals in institutional care who have dysphagia and aspiration. The economic burden of the clinical consequences arising from lack of diagnosis and early management of dysphagia are therefore significant.

As noted, pneumonia is a common clinical consequence of dysphagia. Pneumonia may require acute hospitalisation and emergency room visits. Among those that develop pneumonia due to aspiration, the differential diagnosis of ‘aspiration pneumonia’ is not necessarily indicated as a result of current care practices. Based on U.S. healthcare utilisation surveys from recent years, pneumonia accounted for over one million hospital discharges and an additional 392,000 were attributable to aspiration pneumonia. Individuals who have general pneumonia as the principal diagnosis have a mean 6 day hospital length of stay and incur over $18,000 in costs for hospital care. It is expected that aspiration pneumonia would carry higher costs for hospital care, based on a mean 8 day length of hospital stay. Pneumonia is life threatening among persons with dysphagia, the odds of death within 3 months is about 50% (van der Steen et al. 2002). In addition, an acute insult such as pneumonia often initiates the downward spiral in health among elderly. An insult is associated with poor intakes and inactivity, resulting in malnutrition, functional decline, and frailty. Specific interventions (e.g., to promote oral health, help restore normal swallow, or reinforce a swallow-safe bolus) would benefit persons at risk for (due to aspiration of oropharyngeal contents, including silent aspiration) or experiencing recurrent pneumonia.

Similar to pneumonia, dehydration is a life-threatening clinical complication of dysphagia. Dehydration is a common co-morbidity among hospitalised individuals with neurodegenerative diseases (thus, likely to have a swallowing impairment). The conditions of Alzheimer’s disease, Parkinson’s disease, and multiple sclerosis account for nearly 400,000 U.S. hospital discharges annually, and up to 15% of these patients suffer dehydration. Having dehydration as the principal diagnosis is associated with a mean 4 day length of hospital stay and over $11,000 in costs for hospital care. Nevertheless, dehydration is an avoidable clinical complication of dysphagia.

Malnutrition and related complications (e.g., [urinary tract] infections, pressure ulcers, increased severity of dysphagia [need for more-restricted food options, tube feeding, and/or PEG placement and reduced quality of life], dehydration, functional decline and related consequences [falls, dementia, frailty, loss of mobility, and loss of autonomy]) can arise when swallowing impairment leads to fear of choking on food and liquids, slowed rate of consumption, and self-limited food choices. If uncorrected, inadequate nutritional intake exacerbates dysphagia as the muscles that help facilitate normal swallow weaken as physiological reserves are depleted. Malnutrition is associated with having a more than 3-times greater risk of infection. Infections are common in individuals with neurodegenerative diseases (thus, likely to have a chronic swallowing impairment that jeopardizes dietary adequacy). The conditions of Alzheimer’s disease, Parkinson’s disease, and multiple sclerosis account for nearly 400,000 U.S. hospital discharges annually, and up to 32% of these patients suffer urinary tract infection.

Malnutrition has serious implications for patient recovery. Malnourished patients have longer length of hospital stay, are more likely to be re-hospitalised, and have higher costs for hospital care. Having malnutrition as the principal diagnosis is associated with a mean 8 day length of hospital stay and nearly $22,000 in costs for hospital care. Furthermore, malnutrition leads to unintentional weight loss and predominant loss of muscle and strength, ultimately impairing mobility and the ability to care for oneself. With the loss of functionality, caregiver burden becomes generally more severe, necessitating informal caregivers, then formal caregivers, and then institutionalisation. However, malnutrition is an avoidable clinical complication of dysphagia.

Among persons with neurodegenerative conditions (e.g., Alzheimer’s disease), unintentional weight loss (a marker of malnutrition) precedes cognitive decline. In addition, physical activity can help stabilize cognitive health. Thus, it is important to ensure nutritional adequacy among persons with neurodegenerative conditions to help them have the strength and endurance to participate in regular therapeutic exercise and guard against unintentional weight loss, muscle wasting, loss of physical and cognitive functionality, frailty, dementia, and progressive increase in caregiver burden.

Falls and related injuries are a special concern among elderly with neurodegenerative conditions, associated with loss of functionality. Falls are the leading cause of injury deaths among older adults. Furthermore, fall-related injuries among elderly accounted for more than 1.8M U.S. emergency room visits in a recent year. Direct medical costs totaled $179M for fatal and $19.3 B for nonfatal fall-related injuries in the period of a year. As an effect of an ambitious non-payment for performance initiative introduced in U.S. hospitals in October 2008, Medicare will no longer pay hospitals for treatment cost of falls and related injuries that occur during the hospital stay. Hospitals will face a loss of about $50,000 for each elderly patient who falls and suffers hip fracture while in hospital care. This new quality initiative is based on the premise that falls are an avoidable medical error. In other words, falls are preventable within reason by applying evidence-based practices including medical nutrition therapy as nutritional interventions are efficacious in the prevention of falls and related injuries (e.g., fractures) among the elderly.

Chewing and swallowing difficulties are recognised risk factors for pressure ulcer development. Pressure ulcers are considered an avoidable medical error, preventable within reason by applying evidence-based practices (including nutritional care, as pressure ulcers are more likely when nutrition is inadequate). Pressure ulcers are a significant burden to the health care system. In U.S. hospitals in 2006, there were 322,946 cases of medical error connected with pressure ulcer development. The average cost of healing pressure ulcers depends on the stage, ranging from about $1,100 (for stage II) to about $10,000 (for stage III & IV pressure ulcers). Thus, the estimated cost of healing the cases of medical error connected with pressure ulcer development in one year, is in the range of $323M to $3.2 B. As an effect of an ambitious non-payment for performance initiative introduced in U.S. hospitals in October 2008, Medicare will no longer pay hospitals for treatment cost of pressure ulcers that develop during the hospital stay (up to $3.2 B annually). Pressure ulcers are preventable within reason, in part, by assuring nutritional intakes are adequate. Furthermore, specific interventions including the use of specialised nutritional supplements help reduce the expected time to heal pressure ulcers once they've developed.

In U.S. long-term care facilities, quality of care standards are enforced via the frequent regulatory survey. Surveyors will consider facilities out of compliance when they uncover evidence of actual or potential harm/negative outcomes. The range of penalties includes fines, forced closure, as well as lawsuits and settlement fees. The Tag F325 (nutrition) survey considers significant unplanned weight change, inadequate food/fluid intake, impairment of anticipated wound healing, failure to provide a therapeutic diet as ordered, functional decline, and fluid/electrolyte imbalance as evidence for providing sub-standard nutritional care. The Tag F314 (pressure ulcers) survey mandates that the facility must ensure that a resident who is admitted without pressure ulcers does not develop pressure ulcers unless deemed unavoidable. In addition, that a resident having pressure ulcers receives necessary treatment and services to promote healing, prevent infection and prevent new pressure ulcers from developing.

Therefore considering the prevalence of dysphagia and the possible complications related thereto, and the costs associated with same, it would be beneficial to provide nutritional products that promote safer swallowing of boluses of the nutritional products in individuals who suffer from dysphagia. Such nutritional products would improve the lives of a large and growing number of individuals who suffer from dysphagia. Specific interventions (e.g., to promote oral health, help restore normal swallowing, or reinforce a swallow-safe bolus) can enable individuals to eat orally as opposed to being tube fed and/or requiring PEG placement) and experience the psycho-social aspects of nutritional products associated with general well-being while guarding against the potentially negative consequences that result from lack of adequate swallowing ability. Improvements in the intake of nutritional products by individuals who suffer from dysphagia may also enable such individuals to swallow a wider variety of nutritional products safely and comfortably, which may lead to an overall healthier condition of the individual and prevent further health-related decline.

There is therefore a need to overcome the aforementioned drawbacks and to provide natural cohesiveness that saliva provides to food boluses of nutritional products when being consumed by an individual.

SUMMARY OF INVENTION

The present disclosure is related to nutritional products, a use of the nutritional products, a method for making the nutritional products and a method for improving the cohesiveness of the nutritional products.

In a first aspect the present invention relates to a nutritional product. The nutritional product comprises an aqueous solution which comprises beta-glucan in a concentration of from 0.01 wt % to 10 wt %. The aqueous solution is capable of providing to the nutritional product a shear viscosity of preferably less than 200 mPas when measured at a shear rate of 50 $s^{-1}$. Furthermore the aqueous solution is capable of providing to the nutritional product a relaxation time that can be determined by a Capillary Breakup Extensional Rheometry (CaBER) experiment of preferably more than 10 ms (milliseconds) at a temperature of typically about 20° C.

In a further aspect the nutritional product is used for treating a swallowing disorder in a patient in need of such treatment.

In a further aspect the nutritional product is used for promoting safe swallowing of nutritional products in a patient in need of same.

In a further aspect the nutritional product is used for mitigating the risks of aspiration during swallowing of nutritional products in a patient in need of same.

In a further aspect the present invention relates to a method for making a nutritional product. The method comprising providing an aqueous solution comprising beta-glucan in a concentration of from 0.01 wt % to 10 wt % capable of providing to the nutritional product: a shear viscosity of preferably less than 200 mPas when measured at a shear rate of 50 $s^{-1}$, and a relaxation time, determined by a Capillary Breakup Extensional Rheometry (CaBER) experiment, of preferably more than 10 ms (milliseconds) at a temperature of typically about 20° C.

In a further aspect the present invention relates to a method for improving the cohesiveness of a nutritional product. The method comprising adding to a nutritional product an aqueous solution comprising beta-glucan in a concentration of from 0.01 wt % to 10 wt % capable of providing to the nutritional product: a shear viscosity of preferably less than 200 mPas when measured at a shear rate of 50 $s^{-1}$, a relaxation time, determined by a Capillary Breakup Extensional Rheometry (CaBER) experiment, of preferably more than 10 ms (milliseconds) at a temperature of typically about 20° C.

The further embodiments describe the preferred aspects of the present invention.

DETAILED DESCRIPTION

For a complete understanding of the present invention and the advantages thereof, reference is made to the following detailed description.

It should be appreciated that the various aspects and embodiments of the detailed description as disclosed herein are illustrative of the specific ways to make and use the invention and do not limit the scope of invention when taken into consideration with the claims and the detailed description. It will also be appreciated that features from aspects and embodiments of the invention may be combined with further features from the same or different aspects and embodiments of the invention.

As used in this detailed description and the appended claims, the singular forms "a," "an" and "the" include plural referents unless the context clearly dictates otherwise.

All ranges described are intended to include all numbers, whole or fractions, contained within the said range.

In a first aspect the present invention relates to a nutritional product. The nutritional product comprises an aqueous solution which comprises beta-glucan in a concentration of from 0.01 wt % to 10 wt %. The aqueous solution is capable of providing to the nutritional product a shear viscosity of preferably less than 200 mPas, when measured at a shear rate of 50 $s^{-1}$. Furthermore the aqueous solution is capable of providing to the nutritional product a relaxation time that is determined by a Capillary Breakup Extensional Rheometry (CaBER) experiment of preferably more than 10 ms (milliseconds) at a temperature of typically about 20° C.

The nutritional product refers to nutritional compositions for oral administration by an individual who suffers from dysphagia. The nutritional product is envisaged for supplemental nutrition or for replacement of one or more full meals of the individual who suffers from dysphagia. The nutritional product is moreover understood to include any number of optional ingredients. The optional ingredients including conventional food additives, for example one or more, acidulants, additional thickeners, buffers or agents for pH adjustment, chelating agents, colorants, emulsifiers, excipient, flavour agent, minerals, osmotic agents, a pharmaceutically acceptable carrier, preservatives, stabilisers, sugar(s), sweetener(s), texturiser(s), and/or vitamin(s). The optional ingredients can be added in any suitable amount.

The term individual refers to any human, animal, mammal or who suffers from dysphagia that can benefit from the nutritional product. It is to be appreciated that animal includes, but is not limited to, mammals. Mammal includes, but is not limited to, rodents, aquatic mammals, domestic animals such as dogs and cats, farm animals such as sheep, pigs, cows and horses, and humans.

In the present invention, beta-glucan (β-glucan) refers to homopolysaccharides of D-glucopyranose monomers linked by (1→3), (1→4)-β-glycosidic bonds. Beta-glucan is derivable from plant or microbial origin, e.g. from oat or barley, by methods known to the skilled person, for example as described by Lazaridou et al. in 'A comparative study on structure-function relations of mixed-linkage (1→3), (1→4) linear β-D-glucans' in Food Hydrocolloids, 18 (2004), 837-855.

Beta-glucan and hence also oat shows particularly preferable properties in the inventive compositions as it allows to provide with small amounts of beta-glucan the claimed higher shear viscosities of less than 200 mPas, preferably less than 200 mPas and above 100 mPas, more preferably between 100 and 200 mPas, all when measured at a shear rate of 50 $s^{-1}$, and relaxation times of more than 10 milliseconds, preferably as determined by a CABER experiment at a temperature of 20° C. as described in the present invention.

As used herein, wt % refers to the weight of a particular feature per total weight.

As used herein the feature bolus includes any entity of the nutritional product formed in the mouth in preparation for swallowing. The bolus may be of any size, composition and/or texture. It is preferably a liquid.

Shear viscosity of products is determined by any method that can accurately control the shear rate applied to the product and simultaneously determine the shear stress or vice versa. Standard methods include the use of concentric cylinders, cone-and-plate and plate-plate geometries. Relaxation times can be determined in this context by a Capillary Breakup Extensional Rheometry (CaBER) as further outlined below.

Shear viscosity is a measurable rheological property. Shear viscosity, often referred to as viscosity, describes the action of a material to applied shear stress. In other words, shear stress is the ratio between "stress" (force per unit area) exerted on the surface of a fluid, in the lateral or horizontal direction, to the change in velocity of the fluid as you move down in the fluid (a "velocity gradient").

Another rheological property of a material is its extensional viscosity. Extensional viscosity is the ratio of the stress required to extend a liquid in its flow direction to the extension rate. Extensional viscosity coefficients are widely used for characterising polymers, where they cannot be simply calculated or estimated from the shear viscosity. Rheological studies are generally performed using rheometers, which generally impose a specific stress field or deformation to the fluid and monitor the resultant deformation or stress. These instruments may operate in steady flow or oscillatory flow, as well as both shear and extension.

The Capillary Breakup Extensional Rheometer (CaBER) is an example for a rheometer applying extensional stress. During the CaBER experiment as performed herein for measuring the relaxation time of the nutritional product, a drop of said product is placed between two vertically aligned and parallel circular metal surfaces, both having a diameter of 6 mm. The metal surfaces are then rapidly separated linearly over a time interval of 50 ms (milliseconds). The filament formed by this stretching action subsequently thins under the action of interfacial tension and the thinning process is followed quantitatively using a digital camera and/or laser sheet measuring the filament diameter at its mid-point. The relaxation time in a CaBER experiment is determined by plotting the normalised natural logarithm of the filament diameter during the thinning process versus time and determining the slope of the linear portion ($d_{ln}(D/D_o)/d_t$) of this curve, where D is the filament diameter, $D_o$ the filament diameter at time zero and t the time of filament thinning. The relaxation time in this context is then defined as minus one third (−⅓) times the inverse of this slope, i.e. $-1/(3d_{ln}(D/D_o)/d_t)$.

Typically, the nutritional product according to the invention has a shear viscosity of less than 300 mPas, when measured at a shear rate of 50 $s^{-1}$, preferably of less than 200 mPas, when measured at a shear rate of 50 $s^{-1}$. In this context, the nutritional product according to the invention may have a shear viscosity from 0.1 to 300 mPas, a shear viscosity from 10 to 300 mPas, a shear viscosity from 25 to 300 mPas, a shear viscosity from 50 to 300 mPas, a shear viscosity from 75 to 300 mPas, and preferably a shear viscosity from 100 or above 100 to 300 mPas, e.g. from 100.01 to 300 mPas, a shear viscosity from 125 to 300 mPas, or a shear viscosity of from 150 to 300 mPas, all shear viscosities measured at a shear rate of 50 $s^{-1}$. Likewise preferred or even more preferably the nutritional product according to the invention may have a shear viscosity of less than 200 mPas, when measured at a shear rate of 50 $s^{-1}$, e.g.

a shear viscosity from 0.1 to 200 mPas, a shear viscosity from 10 to 200 mPas, a shear viscosity from 25 to 200 mPas, a shear viscosity from 50 to 200 mPas, a shear viscosity from 75 to 200 mPas, however, more preferably a shear viscosity from 100 to 200 mPas or between 100 and 200 mPas, e.g. from 100.01 to 200 mPas, a shear viscosity from 125 to 200 mPas, a shear viscosity from 150 to 200 mPas, or a shear viscosity from 110 to 160 mPas, all shear viscosities measured at a shear rate of 50 $s^{-1}$.

It is preferred that in the present nutritional product of the invention, the relaxation time is less than 2000 ms, preferably from 20 ms to 1000 ms, likewise preferably from 50 ms to 500 ms, and more preferably from 50 ms to 200 ms, each at a temperature of 20° C. Even more preferably the relaxation time is between 75 ms to 200 ms at a temperature of 20° C. or most preferably even between 75 ms to 150 ms at a temperature of 20° C.

Moreover, in a preferred embodiment of the present invention, a filament diameter of the nutritional product decreases less than linearly, and preferably exponentially in time during the CaBER experiment. The filament diameter can be measured using a digital camera and/or laser sheet measuring device.

In the nutritional product of the present invention, it is preferred that the aqueous solution comprises beta-glucan in a concentration of from at least 0.01 wt % to 10 wt %, preferably from at least 0.1 wt % to 7.5 wt %, and most preferably from at least 1 wt % to 5 wt %, likewise preferably e.g. from at least 0.1 wt % to 10 wt %, from at least 1 wt % to 10 wt %, from at least 5 wt % to 10 wt % or from at least 2.5 wt % to 7.5 wt %.

In a further embodiment the nutritional product is in an aqueous diluted form. In this regards the nutritional products in the aqueous dilution ranges from 2:1 to 50:1, more preferably from 3:1 to 20:1 and most preferably from 5:1 to 10:1. It is to be understood that a dilution of 2:1 means 2 parts of water:1 part of nutritional product.

The nutritional product according to the invention may furthermore comprise one or more of at least one protein, a source of fat, at least one fibre, a source of carbohydrate, a prebiotic, a probiotic, an amino acid, a fatty acid, a phytonutrient, an antioxidant, and/or combinations thereof.

In a further embodiment of the present invention, the nutritional product comprises at least one protein. The at least one protein can be a dairy based protein, a plant based protein or an animal based protein or any combination thereof. Dairy based proteins include, for example, casein, caseinates (e.g., all forms including sodium, calcium, potassium caseinates), casein hydrolysates, whey (e.g., all forms including concentrate, isolate, demineralized), whey hydrolysates, milk protein concentrate, and milk protein isolate. Plant based proteins include, for example, soy protein (e.g., all forms including concentrate and isolate), pea protein (e.g., all forms including concentrate and isolate), canola protein (e.g., all forms including concentrate and isolate), other plant proteins that commercially are wheat and fractionated wheat proteins, corn and it fractions including zein, rice, oat, potato, peanut, green pea powder, green bean powder, and any proteins derived from beans, lentils, and pulses. Animal based proteins may be selected from the group consisting of beef, poultry, fish, lamb, seafood, or combinations thereof.

In a further embodiment of the present invention, the nutritional product comprises a source of fat. The source of fat includes, vegetable fat (such as olive oil, corn oil, sunflower oil, rapeseed oil, hazelnut oil, soy oil, palm oil, coconut oil, canola oil, lecithins, and the like), animal fats (such as milk fat) or any combinations thereof.

In a further embodiment of the present invention, the nutritional product comprises fibre or a fibre blend. The fibre blend may contain a mixture of soluble and insoluble fibre. Soluble fibres may include, for example, fructooligosaccharides, acacia gum, inulin, etc. Insoluble fibres may include, for example, pea outer fibre.

In a further embodiment of the present invention, the nutritional product comprises a source of carbohydrate. The source of carbohydrate includes sucrose, lactose, glucose, fructose, corn syrup solids, maltodextrin, modified starch, amylose starch, tapioca starch, corn starch or any combinations thereof. Inclusion of carbohydrates are advantageous inter alia to allow a simple preparation of the nutritional product, e.g. in form of a dispersion of a powder, etc.

In a further embodiment, the nutritional product comprises at least one the following prebiotics, or any combination thereof: acacia gum, alpha glucan, arabinogalactans, dextrans, fructooligosaccharides, fucosyllactose, galactooligosaccharides, galactomannans, gentiooligosaccharides, glucooligosaccharides, guar gum, inulin, isomalto-oligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, or their hydrolysates, or combinations thereof. The prebiotic is a food substance that selectively promotes the growth of beneficial bacteria or inhibits the growth or mucosal adhesion of pathogenic bacteria in the intestines. The prebiotic are not inactivated in the stomach and/or upper intestine or absorbed in the gastrointestinal tract of the individual ingesting them, but they are fermented by the gastrointestinal microflora and/or by probiotics. Prebiotics are, for example, defined by Glenn R. Gibson and Marcel B. Roberfroid, Dietary Modulation of the Human Colonic Microbiota: Introducing the Concept of Prebiotics, J. Nutr. 1995 125: 1401-1412.

In a further embodiment, the nutritional product comprises at least one probiotic. Probiotics are food-grade microorganisms (alive, including semi-viable or weakened, and/or non-replicating), metabolites, microbial cell preparations or components of microbial cells that could confer health benefits on a host when administered, more specifically probiotics beneficially affect the host by improving intestinal microbial balance, leading to effects on the health or well-being of the host. See, Salminen S, Ouwehand A. Benno Y. et al., Probiotics: how should they be defined?, Trends Food Sci. Technol. 1999: 10, 107-10. In general, it is believed that these probiotics inhibit or influence the growth and/or metabolism of pathogenic bacteria in the intestinal tract. The probiotics may also activate the immune function of the host. The probiotics used in the present invention include *Aerococcus, Aspergillus, Bacillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or any combination thereof.

The nutritional product may comprise a synbiotic. A synbiotic is a supplement that comprises both a prebiotic (at least one of the aforementioned) and a probiotic (at least one of the aforementioned) that work together to improve the microflora of the intestine.

In a further embodiment, the nutritional product comprises at least one the following amino acids, or any combination thereof: alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine and valine.

In a further embodiment, the nutritional product comprises at least one fatty acid or any combination thereof. The fatty acid includes ω-3 fatty acids such α-linolenic acid ("ALA"), docosahexaenoic acid ("DHA") and eicosapentaenoic acid ("EPA"). The fatty acid is derivable from fish oil, krill, poultry, eggs, a plant source, algae and a nut source. The nut source includes flax seed, walnuts, almonds.

In a further embodiment, the nutritional product comprises at least one phytonutrient. The phytonutrient is at least one of flavanoids, allied phenolic compounds, polyphenolic compounds, terpenoids, alkaloids, sulphur-containing compounds.

Phytonutrient are non-nutritive compounds that are found in many foods. Phytonutrients are functional foods that have health benefits beyond basic nutrition, and are health promoting compounds that come from plant sources. Phytonutrient refers to any chemical produced by a plant that imparts one or more health benefit on a user. Non-limiting examples of phytonutrients include those that are:

i) phenolic compounds which include monophenols (such as, for example, apiole, carnosol, carvacrol, dillapiole, rosemarinol); flavonoids (polyphenols) including flavonols (such as, for example, quercetin, fingerol, kaempferol, myricetin, rutin, isorhamnetin), flavanones (such as, for example, fesperidin, naringenin, silybin, eriodictyol), flavones (such as, for example, apigenin, tangeritin, luteolin), flavan-3-ols (such as, for example, catechins, (+)-catechin, (+)-gallocatechin, (−)-epicatechin, (−)-epigallocatechin, (−)-epigallocatechin gallate (EGCG), (−)-epicatechin 3-gallate, theaflavin, theaflavin-3-gallate, theaflavin-3'-gallate, theaflavin-3,3'-digallate, thearubigins), anthocyanins (flavonals) and anthocyanidins (such as, for example, pelargonidin, peonidin, cyanidin, delphinidin, malvidin, petunidin), isoflavones (phytoestrogens) (such as, for example, daidzein (formononetin), genistein (biochanin A), glycitein), dihydroflavonols, chalcones, coumestans (phytoestrogens), and Coumestrol; Phenolic acids (such as: Ellagic acid, Gallic acid, Tannic acid, Vanillin, curcumin); hydroxycinnamic acids (such as, for example, caffeic acid, chlorogenic acid, cinnamic acid, ferulic acid, coumarin); lignans (phytoestrogens), silymarin, secoisolariciresinol, pinoresinol and lariciresinol); tyrosol esters (such as, for example, tyrosol, hydroxytyrosol, oleocanthal, oleuropein); stilbenoids (such as, for example, resveratrol, pterostilbene, piceatannol) and punicalagins.

ii) terpenes (isoprenoids) which include carotenoids (tetraterpenoids) including carotenes (such as, for example, α-carotene, β-carotene, γ-carotene, δ-carotene, lycopene, neurosporene, phytofluene, phytoene), and xanthophylls (such as, for example, canthaxanthin, cryptoxanthin, aeaxanthin, astaxanthin, lutein, rubixanthin); monoterpenes (such as, for example, limonene, perillyl alcohol); saponins; lipids including: phytosterols (such as, for example, campesterol, beta sitosterol, gamma sitosterol, stigmasterol), tocopherols (vitamin E), and γ-3, -6, and -9 fatty acids (such as, for example, gamma-linolenic acid); triterpenoid (such as, for example, oleanolic acid, ursolic acid, betulinic acid, moronic acid)

iii) betalains which include Betacyanins (such as: betanin, isobetanin, probetanin, neobetanin); and betaxanthins (non glycosidic versions) (such as, for example, indicaxanthin, and vulgaxanthin).

iv) organosulfides, which include, for example, dithiolthiones (isothiocyanates) (such as, for example, sulphoraphane); and thiosulphonates (allium compounds) (such as, for example, allyl methyl trisulfide, and diallyl sulfide), indoles, glucosinolates, which include, for example, indole-3-carbinol; sulforaphane; 3,3'-diindolylmethane; sinigrin; allicin; alliin; allyl isothiocyanate; piperine; syn-propanethial-S-oxide.

v) protein inhibitors, which include, for example, protease inhibitors vi) other organic acids which include oxalic acid, phytic acid (inositol hexaphosphate); tartaric acid; and anacardic acid.

In a further embodiment, the nutritional product comprises at least one antioxidant. Antioxidants are molecules capable of slowing or preventing the oxidation of other molecules. The antioxidant can be any one of astaxanthin, carotenoids, coenzyme Q10 ("CoQ10"), flavonoids, glutathione Goji (wolfberry), hesperidin, lactowolfberry, lignan, lutein, lycopene, polyphenols, selenium, vitamin A, vitamin C, vitamin E, zeaxanthin, or any combinations thereof.

The nutritional product of the present invention is preferably in an administrable form. The administrable form can be any one of a pharmaceutical formulation, a nutritional formulation, a dietary supplement, a functional food and a beverage product, or any combinations thereof.

The optional ingredients such as the mineral(s) includes boron, calcium, chromium, copper, iodine, iron, magnesium, manganese, molybdenum, nickel, phosphorus, potassium, selenium, silicon, tin, vanadium, zinc, or any combinations thereof.

The optional ingredients such as vitamin(s) includes vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), vitamin C, vitamin D, vitamin E, vitamin K, folic acid and biotin) essential in amounts for normal growth and activity of the body, or any combinations thereof.

In a further aspect, the nutritional product according the invention is used for treating a swallowing disorder in a patient in need of such treatment.

As used herein the terms treating, treatment, treat and alleviate include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms treating, treatment, treat and alleviate also refer to the maintenance and/or promotion of health in an individual not suffering from a disease but who may be susceptible to the development of an unhealthy condition, such as nitrogen imbalance or muscle loss. The terms treating, treatment, treat and alleviate are also intended to include the potentiation or otherwise enhancement of one or more primary prophylactic or therapeutic measure. The terms treating, treatment, treat and alleviate are further intended to include the dietary management of a disease or condition or the dietary management for prophylaxis or prevention a disease or condition.

In a further aspect, the nutritional product according the invention is used for promoting safe swallowing of nutritional products in a patient in need of same.

In a further aspect, the nutritional product according the invention is used for mitigating the risks of aspiration during swallowing of nutritional products in a patient in need of same.

In a further aspect the present invention relates to a method for making the nutritional product. The method comprises providing an aqueous solution comprising beta-glucan in a concentration of from 0.01 wt % to 25 wt % capable of providing to the nutritional product: a shear viscosity of less than 200 mPas, when measured at a shear rate of 50 $s^{-1}$, a relaxation time, determined by a Capillary Breakup Extensional Rheometry (CaBER) experiment, of more than 10 ms (milliseconds) at a temperature of 20° C.

In a further aspect the present invention relates to a method for improving the cohesiveness of a nutritional product. The method comprising adding to a nutritional product an aqueous solution comprising beta-glucan in a concentration of from 0.01 wt % to 25 wt % capable of providing to the nutritional product: a shear viscosity of less than 200 mPas, when measured at a shear rate of 50 $s^{-1}$, a relaxation time, determined by a Capillary Breakup Extensional Rheometry (CaBER) experiment, of more than 10 ms (milliseconds) at a temperature of 20° C.

In an embodiment of the method for improving the cohesiveness of the nutritional product, the nutritional product has a shear viscosity of typically less than 200 mPas, preferably less than 150 mPas, when measured at a shear rate of 50 $s^{-1}$. In a further aspect the nutritional product has a shear viscosity of less than 100 mPas, when measured at a shear rate of 50 $s^{-1}$. In a further aspect the nutritional product has a shear viscosity of less than 50 mPas, when measured at a shear rate of 50 $s^{-1}$. Most preferably, the nutritional product has a shear viscosity as outlined above for the nutritional product.

In an embodiment of the method for improving the cohesiveness of the nutritional product, the nutritional product has a shear viscosity of at least 1 mPas, preferably from at least 1 mPas to less than 50 mPas, and more preferably from at least 5 mPas to less than 20 mPas, when measured at a shear rate of 50 $s^{-1}$.

In an embodiment of the method for improving the cohesiveness of the nutritional product, the relaxation time is less than 2000 ms, preferably from 20 ms to 1000 ms, likewise preferably from 50 ms to 500 ms, and more preferably from 50 ms to 200 ms, each at a temperature of 20° C. Even more preferably the relaxation time is between 75 ms to 200 ms at a temperature of 20° C. or most preferably even between 75 ms to 150 ms at a temperature of 20° C.

In an embodiment of the method for improving the cohesiveness of the nutritional product, a filament diameter of the nutritional product decreases less than linearly, and preferably exponentially in time during the CaBER experiment.

In an embodiment of the method for improving the cohesiveness of the nutritional product, it is preferred that the aqueous solution comprises beta-glucan in a concentration of from at least 0.01 wt % to 25 wt %, preferably from at least 0.1 wt % to 15 wt %, and most preferably from at least 1 wt % to 10 wt %.

In an embodiment of the method for improving the cohesiveness of the nutritional product, it is preferred that the nutritional product is in an aqueous diluted form. In this regards the nutritional products in an aqueous dilution ranging from 2:1 to 50:1, more preferably from 3:1 to 20:1 and most preferably from 5:1 to 10:1. It is to be understood that a dilution of 2:1 means 2 parts of water:1 part of nutritional product.

In an embodiment of the method for improving the cohesiveness of the nutritional product, the method further comprises adding one or more of at least one protein, a source of fat, at least one fibre, a source of carbohydrate, a prebiotic, a probiotic, an amino acid, a fatty acid, a phytonutrient, an antioxidant, and/or combinations thereof.

In an embodiment of the method for improving the cohesiveness of the nutritional product, at least one protein is added to the nutritional product. The at least one protein can be a dairy based protein, a plant based protein or an animal based protein or any combination thereof. Dairy based proteins include, for example, casein, caseinates (e.g., all forms including sodium, calcium, potassium caseinates), casein hydrolysates, whey (e.g., all forms including concentrate, isolate, demineralized), whey hydrolysates, milk protein concentrate, and milk protein isolate. Plant based proteins include, for example, soy protein (e.g., all forms including concentrate and isolate), pea protein (e.g., all forms including concentrate and isolate), canola protein (e.g., all forms including concentrate and isolate), other plant proteins that commercially are wheat and fractionated wheat proteins, corn and it fractions including zein, rice, oat, potato, peanut, green pea powder, green bean powder, and any proteins derived from beans, lentils, and pulses. Animal based proteins may be selected from the group consisting of beef, poultry, fish, lamb, seafood, or combinations thereof.

In an embodiment of the method for improving the cohesiveness of the nutritional product, at least one source of fat is added to the nutritional product. The source of fat includes, vegetable fat (such as olive oil, corn oil, sunflower oil, rapeseed oil, hazelnut oil, soy oil, palm oil, coconut oil, canola oil, lecithins, and the like), animal fats (such as milk fat) or any combinations thereof.

In an embodiment of the method for improving the cohesiveness of the nutritional product, at least one fibre or fibre blend is added to the nutritional product The fibre blend may contain a mixture of soluble and insoluble fibre. Soluble fibres may include, for example, fructooligosaccharides, acacia gum, inulin, etc. Insoluble fibres may include, for example, pea outer fibre.

In an embodiment of the method for improving the cohesiveness of the nutritional product, at least one source of carbohydrate is added to the nutritional product. The source of carbohydrate includes sucrose, lactose, glucose, fructose, corn syrup solids, maltodextrin, modified starch, amylose starch, tapioca starch, corn starch or any combinations thereof.

In an embodiment of the method for improving the cohesiveness of the nutritional product, at least one of the following prebiotics is added to the nutritional product, or any combination thereof: acacia gum, alpha glucan, arabinogalactans, beta-glucan, dextrans, fructooligosaccharides, fucosyllactose, galactooligosaccharides, galactomannans, gentiooligosaccharides, glucooligosaccharides, guar gum, inulin, isomalto-oligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, or their hydrolysates, or combinations thereof. The prebiotic is a food substance that selectively promotes the growth of beneficial bacteria or inhibits the growth or mucosal adhesion of pathogenic bacteria in the intestines. The prebiotic are not inactivated in the stomach and/or upper intestine or absorbed in the gastrointestinal tract of the individual ingesting them, but they are fermented by the gastrointestinal microflora and/or by probiotics. Prebiotics are, for example, defined by Glenn R. Gibson and Marcel B. Roberfroid, Dietary Modulation of the Human Colonic Microbiota: Introducing the Concept of Prebiotics, J. Nutr. 1995 125: 1401-1412.

In an embodiment of the method for improving the cohesiveness of the nutritional product, at least one probiotics is added to the nutritional product. Probiotics are food-grade microorganisms (alive, including semi-viable or weakened, and/or non-replicating), metabolites, microbial cell preparations or components of microbial cells that could confer health benefits on a host when administered, more specifically probiotics beneficially affect the host by improving intestinal microbial balance, leading to effects on the health or well-being of the host. See, Salminen S, Ouwehand A. Benno Y. et al., Probiotics: how should they be defined?, Trends Food Sci. Technol. 1999: 10, 107-10. In general, it is believed that these probiotics inhibit or influence the growth and/or metabolism of pathogenic bacteria in the intestinal tract. The probiotics may also activate the immune function of the host. The probiotics used in the present invention include *Aerococcus, Aspergillus, Bacillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or any combination thereof.

In an embodiment of the method for improving the cohesiveness of the nutritional product, a synbiotic may be added the nutritional product. A synbiotic is a supplement that comprises both a prebiotic (at least one of the aforementioned) and a probiotic (at least one of the aforementioned) that work together to improve the microflora of the intestine.

In an embodiment of the method for improving the cohesiveness of the nutritional product, at least one of the following amino acids may be added the nutritional product: alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine and valine.

In an embodiment of the method for improving the cohesiveness of the nutritional product, at least one fatty acid or any combination thereof may be added the nutritional product. The fatty acid includes ω-3 fatty acids such a-linolenic acid ("ALA"), docosahexaenoic acid ("DHA") and eicosapentaenoic acid ("EPA"). The fatty acid is derivable from fish oil, krill, poultry, eggs, a plant source, algae and a nut source. The nut source includes flax seed, walnuts, almonds.

In an embodiment of the method for improving the cohesiveness of the nutritional product, a phytonutrient may be added the nutritional product. The phytonutrient is at least one of flavanoids, allied phenolic compounds, polyphenolic compounds, terpenoids, alkaloids, sulphur-containing compounds.

Phytonutrient are non-nutritive compounds that are found in many foods. Phytonutrients are functional foods that have health benefits beyond basic nutrition, and are health promoting compounds that come from plant sources. Phytonutrient refers to any chemical produced by a plant that imparts one or more health benefit on a user. Non-limiting examples of phytonutrients include those that are:

vii) phenolic compounds which include monophenols (such as, for example, apiole, carnosol, carvacrol, dillapiole, rosemarinol); flavonoids (polyphenols) including flavonols (such as, for example, quercetin, fingerol, kaempferol, myricetin, rutin, isorhamnetin), flavanones (such as, for example, fesperidin, naringenin, silybin, eriodictyol), flavones (such as, for example, apigenin, tangeritin, luteolin), flavan-3-ols (such as, for example, catechins, (+)-catechin, (+)-gallocatechin, (−)-epicatechin, (−)-epigallocatechin, (−)-epigallocatechin gallate (EGCG), (−)-epicatechin 3-gallate, theaflavin, theaflavin-3-gallate, theaflavin-3'-gallate, theaflavin-3,3'-digallate, thearubigins), anthocyanins (flavonals) and anthocyanidins (such as, for example, pelargonidin, peonidin, cyanidin, delphinidin, malvidin, petunidin), isoflavones (phytoestrogens) (such as, for example, daidzein (formononetin), genistein (biochanin A), glycitein), dihydroflavonols, chalcones, coumestans (phytoestrogens), and Coumestrol; Phenolic acids (such as: Ellagic acid, Gallic acid, Tannic acid, Vanillin, curcumin); hydroxycinnamic acids (such as, for example, caffeic acid, chlorogenic acid, cinnamic acid, ferulic acid, coumarin); lignans (phytoestrogens), silymarin, secoisolariciresinol, pinoresinol and lariciresinol); tyrosol esters (such as, for example, tyrosol, hydroxytyrosol, oleocanthal, oleuropein); stilbenoids (such as, for example, resveratrol, pterostilbene, piceatannol) and punicalagins.

viii) terpenes (isoprenoids) which include carotenoids (tetraterpenoids) including carotenes (such as, for example, α-carotene, β-carotene, γ-carotene, δ-carotene, lycopene, neurosporene, phytofluene, phytoene), and xanthophylls (such as, for example, canthaxanthin, cryptoxanthin, aeaxanthin, astaxanthin, lutein, rubixanthin); monoterpenes (such as, for example, limonene, perillyl alcohol); saponins; lipids including: phytosterols (such as, for example, campesterol, beta sitosterol, gamma sitosterol, stigmasterol), tocopherols (vitamin E), and γ-3, -6, and -9 fatty acids (such as, for example, gamma-linolenic acid); triterpenoid (such as, for example, oleanolic acid, ursolic acid, betulinic acid, moronic acid)

ix) betalains which include Betacyanins (such as: betanin, isobetanin, probetanin, neobetanin); and betaxanthins (non glycosidic versions) (such as, for example, indicaxanthin, and vulgaxanthin).

x) organosulfides, which include, for example, dithiolthiones (isothiocyanates) (such as, for example, sulphoraphane); and thiosulphonates (allium compounds) (such as, for example, allyl methyl trisulfide, and diallyl sulfide), indoles, glucosinolates, which include, for example, indole-3-carbinol; sulforaphane; 3,3'-diindolylmethane; sinigrin; allicin; alliin; allyl isothiocyanate; piperine; syn-propanethial-S-oxide.

xi) protein inhibitors, which include, for example, protease inhibitors xii) other organic acids which include oxalic acid, phytic acid (inositol hexaphosphate); tartaric acid; and anacardic acid.

In an embodiment of the method for improving the cohesiveness of the nutritional product, at least antioxidant or any combination thereof may be added the nutritional product. Antioxidants are molecules capable of slowing or preventing the oxidation of other molecules. The antioxidant can be any one of astaxanthin, carotenoids, coenzyme Q10 ("CoQ10"), flavonoids, glutathione Goji (wolfberry), hesperidin, lactowolfberry, lignan, lutein, lycopene, polyphenols, selenium, vitamin A, vitamin C, vitamin E, zeaxanthin, or any combinations thereof.

In an embodiment of the method for improving the cohesiveness of the nutritional product, the nutritional product is provided in an administrable form. The administrable form can be any one of a pharmaceutical formulation, a nutritional formulation, a dietary supplement, a functional food and a beverage product, or any combinations thereof.

In an embodiment of the method for improving the cohesiveness of the nutritional product, optional ingredients such as the mineral(s) includes boron, calcium, chromium, copper, iodine, iron, magnesium, manganese, molybdenum, nickel, phosphorus, potassium, selenium, silicon, tin, vanadium, zinc, or any combinations thereof can be added.

In an embodiment of the method for improving the cohesiveness of the nutritional product, optional ingredients such as such as vitamin(s) includes vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), vitamin C, vitamin D, vitamin E, vitamin K, folic acid and biotin) essential in amounts for normal growth and activity of the body, or any combinations thereof can be added.

It was surprisingly found that the beta-glucan is capable of enhancing the extensional viscosity and, thus, the cohesiveness (e.g., resistance to break-up) of the nutritional products.

It has been found that the nutritional product according to the present invention promotes safer swallowing of food boluses for individuals who suffer from dysphagia. The nutritional products prevent bolus penetration and aspiration through modification of rheological properties of the nutritional products.

Furthermore the nutritional products of the present invention have cohesiveness akin to saliva produced in the mouth and provide a more natural sensation to individuals who suffer from dysphagia. The nutritional products of the present invention are devoid of a thickened sensation as provided by conventional thickeners as no residue is left in the mouth of the individuals who suffer from dysphagia.

The nutritional products of the present invention have organoleptic properties superior to thickened nutritional products as known in the art.

The nutritional products of the present invention improve the cohesion of food boluses to prevent a food bolus from being broken up into smaller fragments, which may enter the airway or leave unwanted residues in the oropharyngeal and/or esophageal tract during the swallowing process. The present Applicants have surprisingly found that the incorporation of beta-glucan in nutritional products achieves a similar or identical, possibly even enhanced effect of increasing the cohesiveness of the food bolus (e.g., for patients who have compromised secretion of saliva).

Applicants have also found that providing the nutritional products of the invention to individuals who suffer from dysphagia reduces the amount of swallowing effort for individuals who suffer from dysphagia. The Applicants have also found that providing the nutritional products of the invention to individuals who suffer from dysphagia reduces the risk of residue build-up in the oropharyngeal and/or esophageal tracts. The nutritional products of the present invention have increased cohesiveness and provide improved nutritional intake for individuals who suffer from dysphagia by enabling the individuals to swallow a wider variety of food and beverage products safely and comfortably. This is achieved by improving bolus integrity ("cohesiveness") and thus lending confidence to the individuals who suffer from dysphagia that the individual is able to consume a wider range of products. The nutritional improvement achieved by a nutritional product thus leads to an overall healthier condition of the individual and prevent further decline.

The invention improves an individual's ability and efficiency to swallow and, thus, improve the individual's safety through reduced risk of pulmonary aspiration. An efficient swallow may permit greater independence from feeding assistance and/or reduced length of time spent in feeding-assistance during meal consumption. Efficient swallowing also reduces the viscosity of liquids required for safety (e.g., pudding, honey and nectar thickness products) and may also limit the use of texture-modified foods. All of these previously described factors are aimed at improving an individual's quality of life.

EXAMPLES

The initial material used for beta-glucan extraction was commercially available and contains 27 to 29% soluble beta-glucan fibre with a high molecular weight. The powder is reconstituted in hot water (80° C.) under stirring for at least 30 minutes. The soluble beta-glucan fraction is subsequently separated from the insoluble part by strong centrifugation (at a speed of 5000 g). For subsequent use in the nutritional composition, the aqueous solution can be diluted to the required consistency or mixed with other ingredients as desired.

The prepared nutritional compositions comprised an aqueous solution comprising beta-glucan in a concentration of from 0.01 wt % to 10 wt % capable of providing to the nutritional product: a shear viscosity of less than 200 mPas, when measured at a shear rate of 50 $s^{-1}$, and a relaxation time, determined by a Capillary Breakup Extensional Rheometry (CaBER) experiment, of more than 10 ms (milliseconds) at a temperature of 20° C.

The specific characteristics of some of the prepared beta-glucan aqueous solutions are provided in the table below in terms of viscosity at shear rate of 50 $s^{-1}$ and relaxation times:

| Viscosity measured at shear rate of 50 $s^{-1}$ (mPas) | CaBER relaxation time (ms) (measured at a temperature at 20° C.) |
|---|---|
| 4-5 | 15-20 |
| 12-20 | 20-30 |
| 35-45 | 30-50 |
| 70-90 | 70-90 |
| 120-150 | 100-130 |

In view of the above, CaBER relaxation times of 100 to 130 are particularly advantageous, and hence a viscosity below 200 mPas, when measured at shear rate of 50 $s^{-1}$ (mPas), preferably a viscosity below 200 mPas and above 100 mPas, when measured at shear rate of 50 $s^{-1}$ (mPas).

Inventive compositions are therefore highly suitable to provide a significant cohesiveness and solve the underlying problem.

Having thus described the present invention and the advantages thereof, it should be appreciated that the various aspects and embodiments of the present invention as disclosed herein are merely illustrative of specific ways to make and use the invention.

The various aspects and embodiments of the present invention do not limit the scope of the invention when taken into consideration with the appended claims and the forgoing detailed description.

What is desired to be protected by Letters Patent is set forth in the following claims:

The invention claimed is:

1. A method for treating a swallowing disorder in a patient in need thereof, the method comprising administering to the patient a nutritional product comprising an aqueous solution consisting essentially of a beta-glucan in a concentration of from 0.01 wt % to 10 wt % of the aqueous solution, the beta-glucan being homopolysaccharides of D-glucopyranose monomers linked by (1→3), (1→4)-β-glycosidic bonds, and the nutritional product comprises an amount of the beta-glucan effective for providing to the nutritional product (i) a shear viscosity of less than 200 mPas when measured at a shear rate of $50s^{-1}$; and (ii) a relaxation time, determined by a Capillary Breakup Extensional Rheometry (CaBER) experiment, of more than 10 ms (milliseconds) at a temperature of 20° C.

2. The method according to claim 1 for promoting safe swallowing of nutritional products in a patient in need of safe swallowing of the nutritional products.

3. The method according to claim 1 for mitigating the risks of aspiration during swallowing of nutritional products in a patient in need of mitigating the risks of aspiration during swallowing of the nutritional products.

4. The method according to claim 1, wherein the aqueous solution consists of the beta-glucan and at least one additional ingredient selected from the group consisting of an acidulant, a thickener, a buffer or an agent for pH adjustment, a chelating agent, a colorant, an emulsifier, an excipient, a flavor agent, a mineral, an osmotic agent, a pharmaceutically acceptable carrier, a preservative, a stabilizer, a sugar, a sweetener, a texturizer, and a vitamin.

* * * * *